United States Patent [19]

Rush

[11] Patent Number: 5,614,186
[45] Date of Patent: Mar. 25, 1997

[54] INFECTED SOILBORNE FUNGUS FOR INOCULATING PLANTS

[75] Inventor: Charles M. Rush, Amarillo, Tex.

[73] Assignee: Texas A&M University System, College Station, Tex.

[21] Appl. No.: 299,608

[22] Filed: Sep. 1, 1994

[51] Int. Cl.$^6$ .......................... A01N 63/00; A01N 63/04; A01H 5/10; A01G 7/00
[52] U.S. Cl. ..................... 424/93.3; 424/93.5; 424/93.6; 47/57.6; 47/58; 71/1; 435/235.1; 435/243; 435/254.1; 435/254.11; 504/100; 504/117; 800/200
[58] Field of Search ................................. 424/93.5, 93.6, 424/93.3; 800/200; 47/57.6, 58, DIG. 9; 71/1, 6; 504/100, 117; 435/41, 235.1, 243, 254.11

[56] References Cited

U.S. PATENT DOCUMENTS 5,041,290  8/1991  Gindrat et al. ............................ 424/93

FOREIGN PATENT DOCUMENTS

3277273A2  of 1991  Japan .

OTHER PUBLICATIONS

Abe and Tamada, 1986, *Ann. Phytopath. Soc. Japan,* 52:235–247.
Barr, 1979, *CA. J. Plant Pathology,* 1:85–94.
Bouzoubaa et al., 1987, *J. General Virology,* 68:615–626.
Bouzoubaa et al., 1988, In: *Viruses with Fungal Vectors,* JI Cooper, ed, Chapter 7, "Genome Organization of BNYVV," pp. 99–110.
Brunt and Richards, 1989, In: *Advances in Virus Research,* vol. 36, pp. 1–32.
Fauquet et al., 1988, In: *Viruses with Fungal Vectors,* J. I. Cooper, Ed., pp. 19–36.
Haverson & Rush, 1993, *Phytopathology,* 83:1216–1219.
Heidel & Rush, 1994, *Plant Disease,* 78:603–606.
Kaufmann et al., 1992, *Intervirology,* 33:97–102.
Kendall et al., 1988, *J. General Virology,* 69:2335–2345.
Matthews, In: *Plant Virology,* 3d Ed, Academic Press, NY 1991, p. 346.
Prillwitz & Schlosser, 1993, In: Proceedings of the Second Symposium of the International Working Group on Plant Viruses with Fungal Vectors, C. Hiruki, ed, McGill Univ, Montreal, Canada, pp. 71–74.
Putz, 1977, *J. General Virology,* 35:397–401.
Richards and Tamada, 1992, *Ann. Rev. Phytopathol,* 30:291–313.
Sambrook et al., 1989, In: *Molecular Clongin: A Laboratory Manual,* 2d Ed., Cold Spring Harbor Laboratory, NY, Chapter 7.
Shirako and Brake, 1984, *J. General Virology,* 65:119–127.
Tamada et al, 1990, In: Proceedings of the First Symposium of the International Working Group on Plant Viruses with Funal Vectors, R. Koenig, ed, Braunschweig, Germany, pp. 41–44.

*Primary Examiner*—Douglas W. Robinson
*Assistant Examiner*—Elizabeth F. McElwain
*Attorney, Agent, or Firm*—Pravel, Hewitt, Kimball & Krieger

[57] ABSTRACT

A method for conferring plant tolerance to severe diseases, specifically caused by a viruses vectored by soilborne fungi, wherein a non-virulent or mildly virulent virus is transmitted to the plant and renders the plant tolerant to disease caused by a more virulent virus. The protective virus is transmitted to a host plant via a viruliferous soilborne fungus which is coated onto seed and thereby produces a disease tolerant plant.

24 Claims, No Drawings

INFECTED SOILBORNE FUNGUS FOR INOCULATING PLANTS

FIELD OF THE INVENTION

This invention relates to the treatment of plants to reduce the plant's susceptibility to severe disease caused by virulent viral pathogens. Plants inoculated with a non-virulent or mildly virulent virus do not express severe disease symptoms caused by the virulent virus even when coinoculated with the virulent virus. A novel inoculation method includes application of viruliferous fungus to seeds by coating seeds with survival structures of the viruliferous fungus, such as cystsori of polymyxa species.

BACKGROUND OF THE INVENTION

Rhizomania, "root madness" is a severe disease of sugar beet caused by beet necrotic yellow vein virus (BNYVV) and transmitted by the soilborne fungus *Polymyxa betae*. The disease is widely distributed in many countries and is economically devastating to a sugar beet crop, causing severe loss in root yield and sugar content of the infected plants. In naturally infected plants, BNYVV is normally confined to the roots, and causes massive proliferation of the lateral rootlets of taproots as well as other abnormalities of the root system.

Novel isolates of beet soilborne mosaic virus, BSBMV (previously called Texas 7), have now been identified as non-virulent or mildly virulent viruses closely related to BNYVV. When co-inoculated with BNYVV in a susceptible host, BSBMV dominates over BNYVV, and interferes with infection by the more pathogenic BNYVV. A method for preferentially incorporating BSBMV into plants and thereby excluding or inhibiting infection and disease caused by the more virulent BNYVV would be extremely useful, especially in the sugar beet industry. Such a method would also be of great utility for inoculation of plants against a variety of severe diseases caused by furoviruses.

Similarly, a method for easily incorporating a competing, non-virulent or mildly virulent virus into a plant to confer protection against a more virulent pathogen would be highly desirable. Such a method should be easily applied in the field, permit specific application to a plant or field of choice, and be stable over time. The methods of the present invention provide such easily administered and controlled application of a beneficial virus or other desired nucleic acid sequence to a host plant.

SUMMARY OF THE INVENTION

A mildly virulent or non-virulent virus is selectively administered to plants for purposes of reducing or eliminating infection by or disease development caused by a more virulent pathogen. The mildly-virulent or non-virulent virus is transmitted to the plant through a soilborne fungus which is permitted to contact and thereby infest plant seed. Plant seed coated with the viruliferous fungus is stable for long periods of time. When the coated seed is planted in soil, the growing plant becomes infected by the viruliferous fungus which transmits the mildly-virulent or non-virulent virus to the plant. The mildly-virulent or non-virulent virus interferes with the expression of disease symptoms by a more-virulent virus which might otherwise infect the plant, thereby protecting the plant from severe disease.

In a preferred embodiment, the inventive method is used to prevent, delay or reduce BNYVV mediated disease development in sugar beet plants. In a most preferred embodiment, mildly virulent protective virus is BSBMV.

A soilborne fungus, e.g., Polymyxa which transmits both BNYVV and BSBMV, is first infested with a mildly virulent or non-virulent virus, and the viruliferous fungus is then coated onto seed. Most preferably, the seed is coated with a composition containing the viruliferous fungus or with the survival structures of the fungus (e.g., cystosori in Polymyxa) prior to planting the seed in soil.

The seed coating composition preferably consists of dried, powdered roots of a plant infested with a viruliferous soilborne fungus or cystosori of viruliferous fungus, the fungus being infected with the mildly virulent or non-virulent viral isolate.

DETAILED DESCRIPTION OF THE INVENTION

In the method of the present invention, a mildly virulent or non-virulent virus is transmitted to a plant to confer tolerance or resistance to a more virulent viral pathogen. Such protection or interference is conferred by viruses having sufficient similarity and characteristics as the normal virulent virus to be recognized and accepted by the host, yet having less virulent pathogenic characteristics so as to lessen or preclude the disease caused by the virulent virus. For example, BSBMV has much similarity in structure and function to BNYVV, but do not induce the severe symptoms of Rhizomania in plants that are induced by BNYVV.

Mildly Virulent Pathogens

To be useful in the present method invention, a non-virulent or mildly virulent virus is a strain or isolate of a virus, preferably a virus transmitted by a soil fungus, e.g., a furovirus, which shares substrate specificity, binding and functional characteristics with a more virulent strain of a pathogenic virus yet, unlike the pathogenic virus, fails to induce severe disease symptoms in plants. The mildly virulent or non-virulent isolate must also dominate over or interfere with symptom expression of a more virulent, disease-causing virus in a plant susceptible to both viruses, such that infection of a plant by the mildly or non-virulent virus precludes survival and/or effectiveness of the more virulent virus in causing disease in the plant.

To test a sample isolate or strain for utility as a mildly or non-virulent virus in the method of the instant invention, a test virus is directly (e.g., mechanically) inoculated into a plant, preferably alongside mock-innoculated and virulent pathogenic virus-inoculated plant controls. As compared with the virulent virus-inoculated control plant, a mildly or non-virulent virus useful in the present invention will not induce severe disease symptoms in the plant. It is recognized, however, that a mildly-virulent virus may induce some mild disease symptoms, but this does not preclude its utility in the method invention. This is especially true in plant diseases such as Rhizomania, where the virulent virus causes such devastation to sugar beet plants that induction of mild disease symptoms is desirable to prevent great crop loss through the severe disease caused by the virulent pathogen.

The mildly virulent or non-virulent virus must also dominate over the more virulent virus, and inhibit infection or interfere with symptom expression of the more virulent virus in the host plant. To test for this characteristic, a plant is co-inoculated with both the mildly or non-virulent virus (protecting virus) and the more virulent virus, or the plant is first inoculated with the protecting virus, followed by inoculation with the virulent virus. After a period of time to permit virus to infect the plant's system, the plant is assayed for the systemic presence of each virus, e.g., by ELISA.

Alternatively or in combination with the above, the co-inoculated plants are observed for expression of disease symptoms characteristic of the pathogens. To be useful in the present invention, the mildly or non-virulent virus will dominate, or interfere with phenotypic expression of pathogenic disease symptoms of the virulent virus, that is, the disease symptoms caused by the non- or mildly virulent virus are seen in the co-infected plant, and not the severe disease symptoms caused by the more virulent virus.

Representative examples of these assay procedures are found in the Examples described below, which demonstrate the similarities of BSBMV viral isolates to the virulent pathogenic virus BNYVV, known to cause Rhizomania in sugar beet plants. BSBMV is demonstrated to be mildly virulent as compared with BNYVV, causing only mild disease symptoms in plants rather than more severe disease symptoms caused by BNYVV, and show dominance in symptom phenotype over BNYVV when co-inoculated into plants.

It is preferred that the non-virulent or mildly virulent virus be a natural virus, e.g., not a mutated or genetically modified virus. This is to protect against the possibility of reversion of the mutated virus into a more virulent form, thereby causing great harm to the inoculated plant crop and fields. Use of a natural isolate is ecologically preferred over introduction of a foreign, non-indigenous organism into the soil.

BSBMV isolates (also known as Texas 7) are natural virus isolates, found, for example in soil samples from Texas sugar beet-growing counties. See, for example, Heidel and Rush, 1994, *Plant Disease*, 78:603–606. Several BSBMV isolates found in Texas, Nebraska, and California are described in Table 1. These isolates, obtained from plant or soil samples, each tested positive for BSBMV and negative for BNYVV by ELISA and by RT-PCR assay. An example of a BSBMV is BSBMV, on deposit at the American Type Culture Collection and having ATCC Accession No. 75883 BSBMV isolates confer tolerance to disease caused by BNYVV.

TABLE 1

| Isolate | Origin | SYMPTOMS[a] | | RT-PCR PRODUCTS[b] | | Tha I Cleavage |
| --- | --- | --- | --- | --- | --- | --- |
| | | Sugar beet | C. quinoa | BNYVV Primers | BSBMV Primers | |
| BNYVV | Calif. | NFS, RB | YS | 1056 | None | No |
| BSBMV-Neb gfs | Neb. | NRS, SDYB | DCS | 1000 | 700 | Yes |
| BSBMV Neb gh | Neb. | NRS, SDYB | YS | 1000 | 700 | Yes |
| BSBMV-Neb Morrill | Neb. | NRS, SDYB | YS | 1000 | 700 | Yes |
| BSBMV-Harken | Tex. | NRS, SDYB | DCS | 1000 | 700 | Yes |
| BSBMV-NC | Tex. | NRS, SDYB | DCS | 1000 | 700 | Yes |
| BSBMV-FS | Tex. | NRS, SDYB | DCS | 1000 | 700 | Yes |

TABLE 1-continued

[a]Symptoms expressed on the sugar beet for which isolates were originally obtained or on mechanically infected *Chenopodium quinoa*;
NFS = no system is foliar symptoms;
NRS = no obvious root symptoms;
RB = root bearding;
SDYB = systemic diffuse yellow banding on leaves;
YS = yellow spots; and
DCS = diffuse chlorite spots.
[b]Approximate size in base pairs as determined by reserve transcriptase polymerase chain reaction.

In a similar manner, plants may be made tolerany to other diseases caused by viruses vectored soil borne fungus. Examples of such plant diseases caused by the pathogenic viruses listed in Table 10.2 of *Plant Virology*, 3rd Edition, Ref. Matthews, ed, Academic Press, NV, 1991, p. 346.

Soilborne Fungus

In the present invention, a soilborne fungus is used to transmit the non-virulent or mildly-virulent virus to a host plant. Several types of soilborne fungi are known which vector various pathogenic viruses to host plants. Polymyxa, known to vector BNYVV, has now been found to vector BSBMV, a mildly virulent virus which interferes with BNYVV disease expression in co-inoculated plants.

Polymyxa is a member of the family Plasmodiophoraceae and is a ubiquitous soil inhabitant that lives as an obligate parasite on plant roots. The fungus multiplies only within the roots of a host plant. During this multiplicative phase, a plasmodium is formed within the plant cell and can become viruliferous when the host is infected with a virus, i.e., furovirus. The infected plasmodium then differentiates into either a zoosporangium giving rise to new zoospores, or thick-walled resting spores called cystosori. Cystosori, which are released into soil as roots senesece and die, permit the fungus and its infecting virus to survive without a host for long periods of time.

There are two known species of Polymyxa: *P. betae* Keskin and *P. graminis* Ledingham. *P. betae* colonizes plants of the families Chenopodiaceae, Amaranthaceae, and Portulacaceae. *P. graminis* colonizes many grasses. There are at least twelve separate viruses in two taxonomic groups known to be vectored or carried and transmitted into plants by Polymyxa species, including BNYVV by *P. betae* and peanut clump virus (PCV) and wheat spindle streak mosaic virus (WSSMV) by *P. graminis*.

Known furoviruses, defined as rod-shaped viruses with a divided genome which are transmitted by a soil fungus include the following:

soil-borne wheat mosaic virus beet necrotic yellow vein virus beet soil borne virus broad bean necrosis virus fern mottle virus Hyposhoeris mosaic virus peanut clump virus Indian peanut clump virus

*Nicotiana velutina* mosaic virus oat golden stripe virus potato mop-top virus rice stripe necrosis virus (Fauquet et al., 1988, In: *Viruses with Fungal Vectors*, J. I. Cooper, ed, pp. 19–21).

These viruses cause serious disease of several economically important crops, thus their control is of great importance. See, for example, Brunt and Richards, 1989, In: *Advances in Virus Research*, Vol. 36, pp. 1–32.

In a preferred embodiment of the invention, a mildly or non-virulent virus isolate is vectored or carried and transmitted to a plant by a soilborne fungus. The host plant must be susceptible to infection by the soilborne fungus and by the virus it carries. The fungus must be susceptible to infestation by the mildly or non-virulent virus.

Screening of virus-fungus infection and fungus-host plant infestation may be carried out by routine methods known to those of skill in the art. In general, a plant previously artificially inoculated (e.g., by mechanical methods) with a virus is permitted to grow in soil known to contain the specific soilborne fungus to be tested. After permitting the fungus to colonize the roots of the infected plants, the fungus is harvested and analyzed for the presence of the virus, e.g., by directly analyzing the fungal cystosori for the presence of the virus using PCR amplification and hybridization techniques, or indirectly, e.g., by harvesting the cystosori, mixing them with clean soil, and planting in the soil uninfected plants. Fungus then is permitted to colonize the roots of the plants, and the plant is monitored for infection by the transmitted virus by ELISA or by manifestation of mild disease symptoms in the plant known to be induced by the virus.

Coating Seed with Viruliferous Fungus

In a preferred embodiment of the invention, seed of a plant susceptible to a virulent pathogenic virus transmitted by soilborne fungus is coated with a composition containing a viruliferous fungus, the fungus being infected with a mildly-virulent or non-virulent virus. The seed-coating composition contains viruliferous fungus either in the form of fungal resting structures, i.e., cystosori or as infested root material.

Preferably, the cystosori or infested root material is dried, the roots are generally pulverized to powder form. An aqueous slurry of the fungal material is prepared by placing the dried, pulverized fungus material in a solution containing a polymer such as methyl cellulose (e.g., about 0.5–10% by weight). The polymer causes the fungus composition to be "sticky" and to adhere to the seed.

Seed is added to the aqueous slurry of fungal material and mixed until seed is coated. Generally, the slurry is sufficiently fluid to coat the seed on mixing. The coated seed is spread on a surface and permitted to air dry or dried under heat, e.g., in drying ovens. When dry, the seed has an adherent viruliferous fungal coat which is stable upon typical seed storage conditions.

The amount of viruliferous fungus adhered on the seed will vary with the amounts of reagents contained in the slurry. As few as 50–75 seeds may be coated with as much as 400–500 mg of the fungal material. This provides a great advantage for first infecting a growing plant with a desired non-or mildly virulent virus to inhibit or induce tolerance to subsequent infection by a more virulent virus which may be present in the soil.

The inoculum on seeds remains functional for as long as, for example, the cystosori are viable. Studies have shown seed treated approximately two years prior to planting contained infectious inoculum (Harveson & Rush, 1993, *Phytopathology*, 83:1216–1219.

Transmission of Foreign Nucleic Acids

In a preferred embodiment of the present invention, the method of seed-coating with a viruliferous fungus provides an effective and stable method for transmitting a nucleic acid of choice to a host plant. A viruliferous fungus infected with a virus which carries the nucleic acid of choice is coated onto seed of the host plant as described above for a mildly or non-virulent virus. During growth of the seed into a plant, the viruliferous fungus infects the plant and transmits the virus and the nucleic acid of choice to the plant for systemic expression.

Plants are screened by methods known to those of skill in the art for expression of the inserted nucleic acid sequence, e.g., by ELISA.

EXAMPLES

The present invention may be better understood by reference to the following examples, in which BSBMV is characterized as a mildly virulent viral isolate which dominates in co-culture with BNYVV, is transmitted or vectored to host plants by the soilborne fungus *Polymyxa betae*, and confers to host plants resistance or tolerance to more virulent BNYVV infection, thereby protecting host plants from severe Rhizomania. The following are exemplary forms of the invention, and are not intended to limit the scope of the invention.

Example 1

BNYVV TRANSMITTED TO SUGAR BEET PLANTS BY COATING SEED WITH VIRUS-INFECTED SOILBORNE FUNGUS

Preparation of Viruliferous fungus:

BNYVV-infected sugar beet plants were grown in Ray Leach Cone-Tainers (Stuewe and Sons, Inc., Corvallis, Ore.). After 8–12 weeks in the greenhouse, randomly chosen plants were checked microscopically for infection by *P. betae* by looking for the characteristic cystosori of *P. betae* in infected roots under 10× magnification and assayed by enzyme-linked immunosorbent assay (ELISA) for BNYVV infection.

Roots from infected plants were thoroughly washed and allowed to air dry. The dried root tissue was pulverized and separated from soil and other foreign materials by a series of fine-meshed sieves. The resulting product consisted of powdered roots infested with viruliferous cystosori of *P. betae*.

Coating seeds with viruliferous fungus:

Seeds of sugar beet cultivar HH39 (Holly Hybrids, Sheridan, Wyo.) were coated with the powdered root material suspended in 2% methyl cellulose. Two batches of the seed-coating composition were prepared, the first having a ratio of 1:20:20 (w/v/w) of powdered root tissue/2% methyl cellulose/seed, and the second effectively doubling the amount of the powdered root tissue with the ratio being 1:10:10.

Seed was added to the suspension of root inoculum in methyl cellulose, mixed thoroughly, and allowed to air dry.

Growing Plants from Viruliferous-fungus coated seed:

Two to three seeds were planted in each container with a mixture of sand and commercial topsoil. Fifty containers were planted with the *P. betae*-BNYVV-coated seed (1:20:20 ratio) and fifty with control, untreated seed. The containers were kept in a greenhouse at ambient temperature (20°–30° C.) and heavily watered for the first several weeks after planting to initiate early infection. After plants became established, they were watered daily to maintain plant turgor. One-half the plants were harvested after approximately one month and plant tissue was assayed by ELISA for incidence of BNYVV infection. The remaining plants were harvested after approximately two months and assayed for BNYW infection.

The greenhouse study was repeated using the seed-coating composition with the 1:10:10 ratio. Plants were harvested and analyzed for BNYVV at approximately four months after planting.

A field study was conducted in soil that had never before been planted with sugar beets. The test site consisted of two 9 m×30 m plots enclosed on all four sides by a border dike. Each plot contained eight beds with 76 cm spacing, with each bed considered one replication. A single row of untreated seed was planted on the four inside beds of each border. A rate of 15–20 seeds per meter was used to plant the HH39 sugar beet seed at a depth of 2 cm. The two outside beds on each side of the plot were sown in the same manner with the *P. betae*-BNYVV-coated seed (1:20:20 ratio).

The test field was irrigated the same day as planting, followed by three successive irrigations during the season. Irrigation was accomplished by quickly filling the furrows of the enclosed plots until the water reached to just below the top of the beds. The water was allowed time to soak into the beds, then plots were flooded once more. Each bed and furrow was blocked at the end so the irrigation water was contained within each furrow and not allowed access to an adjacent furrow or bed. Each irrigation added approximately 6–8 cm of water.

Analysis of growing plants for the presence of BNYVV was conducted twice during the season by the methods described for the greenhouse study. Ten samples were collected at 3 m intervals from each of the eight rows planted with BNYW-coated seeds. Four to five beets were bulked from one location and constituted a sample. Two random samples were assayed from each of the eight control rows.

The field study was repeated using the seed-coating composition with the 1:10:10 ratio. All parameters were the same, except one less irrigation event. Only one field harvest and ELISA analysis was performed on these plants.

ELISA for BNYVV:

The ELISA assays employed a double antibody sandwich technique using commercially available antisera and enzyme conjugates obtained from Bioreba Ag (Chapel Hill, N.C.) and Agdia (Elkhart, Ind.). Field and greenhouse samples were washed free of soil, and 0.25–0.30 g of root tissue was collected for assay. In addition to the test samples, each 96-well assay plate included four separate healthy control samples, four BNYVV-positive control samples, and four control buffer blanks.

Polyvinyl chloride (PCV) microtiter plates were coated with BNYVV Immunoglobin G (IgG) diluted per the manufacturer's recommendation in 0.1M phosphate-buffered saline (PBS), pH 7.1. Except during the substrate reaction, plates were incubated at 37° C. for one hour. Plates were washed 10 times between steps with wash buffer (0.02M sodium phosphate buffer, pH 7.6, with 0.015M NaCl, 0.05% [V/V] tween-20 and 0.00125% [W/V] thimersol and were incubated in a humidified box. After coating, wells were blocked with wash buffer containing 1% bovine serum albumin (BWB). Except for the blocking step, in which wells were filled, reagent and sample volumes were 50 μl.

Sample extracts were prepared by grinding tissue in BWB (1:10, W/V). Alkaline phosphatase conjugated BNYVV Ig's was diluted according to the manufacturer's recommendation in BWB. Substrate (p-nitrophenyl phosphate, 4.0 mg/ml in 10% diethanolamine, pH 9.8) was added, and plates were incubated in the dark at 25° C. for 1–18 hours, until the positive controls reacted.

Optical density (OD) values at 410 nm were determined using a Dynatech MR300 ELISA microplate reader (Chantilly, Va.). A sample was considered positive if its OD value was at least three times greater than the mean of the four healthy control samples.

Environmental data:

Environmental data was recorded daily by a CR-21 weather station approximately 2 km from the field test site. Data collected included ambient air temperatures, 10-cm soil temperatures, and precipitation. At the time of each planting, the 10 cm soil temperatures were within 22°–27° C. During the first field study, 4 cm of rain fell between planting and final harvest. During the second study, almost 15 cm of rain fell between planting and final harvest.

During both field studies, the 10 cm soil temperatures (approximately 20°–28° C.) were within the range for *P. betae* infection (approximately 15°–30° C.). With the additive effect of rainfall and irrigation (over 30 cm for each planting) there was also adequate moisture for *P. betae* to parasitize the growing sugar beet plants. All environmental conditions were seemingly conducive for infection by *P. betae* and transmission of BNYVV to growing plants.

Results:

At the first harvest, approximately one month after the first planting, 46% of the field samples and 50% of the greenhouse samples were positive for BNYVV. At six weeks after planting, the percentage of BNYVV-positive plants had risen to 57% and 80%, respectively. In the second study, the plants were harvested approximately 3.5 months after planting. Both greenhouse and field plants were 90% positive for BNYVV. In all studies, all of the control samples were negative for BNYVV infection.

TABLE 2

| Study | Place | Harvest | Positives[1] |
|---|---|---|---|
| 1 | Field[2] | 1 month | 46 +/– 18.5 |
| 1 | Field | 1.5 months | 57 +/– 10.5 |
| 2 | Field | 3.5 months | 92 +/– 3.3 |
| 1 | Greenhouse[3] | 1 month | 50 |
| 1 | Greenhouse | 1.5 months | 80 |
| 2 | Greenhouse | 3.5 months | 90 |

[1] Assayed by double antibody sandwich ELISA
[2] Values are mean +/– 2 standard errors of 80 samples (95% confidence interval)
[3] Values represent means of 25 samples Example 2

BNYVV is not rapidly spread in soil by irrigation

Field plots were established to test changes in the distribution of BNYVV-infected *P. betae* over time in fields where soils were artificially infested and to monitor spread of the disease due to irrigation and post harvest soil movement. Rhizomania inoculum, powdered roots of infected plants obtained as described for example 1, was placed in disease-free plots and movement of the pathogen in irrigation water during the growing season and by tillage after harvest was monitored. The ELISA test described for Example 1 was used to determine whether sugar beet plants distant from the source of the inoculum were infected. Samples were analyzed twice during the growing season, approximately 8 weeks after plant emergence and just prior to harvest.

Contrary to expectations, no plants, other than those in the infested soil, tested positive for BNYVV. Soil samples were analyzed immediately before and after harvest and were potted up in the greenhouse to bait out viruliferous *P. betae*. Again, surprisingly, only soil samples from the inoculated areas were positive for BNYVV.

Example 3

BSBMV protects plants from BNYVV infection

*Beta maritima* and *Beta macrocarpa*, which are subspecies of *beta vulgaris* (sugar beet) as well as *Chenopodium quinoa* which is in the same family of plants, are all known to be susceptible to disease caused by BNYVV. BSBMV was tested for its ability to confer in these plants tolerance to BNYW.

Plants were mechanically inoculated with BNYVV, BSBMV or both viruses. The mechanical inoculation method is well known to those of skill in the art. Leaf tissue of an infected plant was ground in buffer and the extract applied with a glass rod to a leaf of a plant to be inoculated. The host plant leaf had been dusted with the abrasive, carborundum. The glass rod and inoculum was rubbed on the leaf, causing uptake of the applied extract inoculum.

Specifically, local lesions of BSBMV or BNYVV on *C. quinoa* were macerated in 0.1M potassium phosphate buffer, pH 7.5, with 0.02M $Na_2SO_3$ and this extract was used to inoculate *C. quinoa*, *B. macrocarpa*, and *B. maritima*. Plants were inoculated with each virus independently or with mixed inoculum. The expression of symptoms of test and control plants was recorded after approximately two weeks, and ELISA tests performed as described for Example 1 were conducted to verify the presence of the viruses in the host plants.

All hosts inoculated with BNYVV alone developed bright yellow local lesions which eventually went systemic in *B. macrocarpa* and *B. maritima*, after which time these plants expired.

*Chenopidium quinoa* inoculated with BSBMV alone developed diffuse, pale yellow local lesions. *B. macrocarpa* and *B. maritima* inoculated with BSBMV alone developed necrotic spots surrounded by purple halos. The BSBMV virus eventually went systemic in *B. maritima* but not in *B. macrocarpa*.

Simultaneous inoculation of both viruses in *C. quinoa* caused a mottled appearance very different from symptoms developed with either virus alone. In *B. macrocarpa* and *B. maritima*, the BSBMV symptom phenotype dominated over the BNYVV phenotype in co-inoculated plants. Mixed infections did not change the systemic reactions of either virus. In mixed infections, none of the plants expressed severe disease symptoms shown in plants infected with BNYVV alone. Thus, infection of plants with BSBMV interfered with expression of severe disease symptoms caused by BNYVV.

Those plants which were inoculated with both BNYVV and BSBMV developed local lesion symptoms of BSBMV only. This indicates that BSBMV interferes with the normal infection process and expression of BNYVV in host plants.

Example 4

Transmission of BSBMV by *P. betae*

Host plants, *Beta maritima*, were mechanically inoculated with BSBMV-FS by the method described for Example 3. After two weeks, roots of the infected plants were inoculated with *P. betae*. Dried root inoculum containing *P. betae* was prepared by obtaining roots from plants infected with *P. betae*. The roots were washed, allowed to dry, pulverized, and separated from soil and other foreign materials by a sercies of fine-meshed sieves. The resulting inoculum consisted of powered roots infested with cystosori of *P. betae*. Host plants were inoculated with the fungus by placing the dried root composition (approximately 0.5 g) in the soil near the roots of the plant. Approximately 10–12 weeks after fungus inoculation, the root tissue was harvested and washed. Dried root tissue was ground to a powder and coated onto sugar beet seed with 2% methyl cellulose as described for Example 1.

Seeds were planted in containers and grown in the greenhouse as described for Example 1. Approximately eight weeks after planting, the root tissue of growing plants are harvested and tested for BSBMV infection by indirect DAS-ELISA as described for Example 4 and visually inspected for cystosori of *P. betae*. Roots were positive for both BSBMV and *P. betae*. These results indicate that BSBMV is transmitted to a host plant via soilborne fungus.

Example 6

Effect of established BSBMV-infected *P. betae* on the spread of BNYVV-infected *P. betae*

Sugar beet plants are grown in small microplots and infected with BSBMV either directly as described for Example 4 or via viruliferous *P. betae* as described for Example 4. The infected beet plants are grown for several weeks to allow a population of *P. betae* infected with BSBMV to become established in the soil. Plant infection by BSBMV is verified by ELISA, after which the plants are removed and the soil in each microplot is mixed to simulate harvest and plowing. Fresh, uninfected beet plants or seeds are planted in the presence or absence of BNYVV inoculum in the soil. Plots without an established BSBMV-infected fungus population are planted as a control. Approximately 8–10 weeks after infesting plots with BYNVV and planting, plants are inspected for phenotypic expression of virus and beets are harvested and evaluated by ELISA for infection by BSBMV and BNYVV.

Example 5

Characterization of BSBMV

BSBMV was compared with BNYVV using PCR to amplify specified regions of each virus, and comparing restriction enzyme digests of each amplified nucleic acid sequence with that of published sequence data from European isolates of BNYVV (Bouzoubaa et al, 1987, *J. Gen. Virol.* 68:615–626.

Preparation of BSBMV:

BSBMV was propagated in *Chenopodium quinoa* Willd. by mechanical inoculation with extract from naturally-infected sugar beet leaf tissue ground in 0.1M potassium phosphate buffer (KPB), pH 7.4, with 0.02M sodium sulfite. BSBMV was purified from symptomatic *C. quinoa* as described by Kendall et al., 1988, *J. Gen. Virol.*, 69:2335–2345 and Shirako & Brakke, 1984, *J. Gen. Virol.*, 65:119–127 with several modifications. 2-mercaptoethanol was added to the grinding buffer to a final concentration of 0.1% (v/v). After the first low-speed centrifugation, the supernatant was strained through Miracloth (Calibiochem, La Jolla, Calif.). After the first high-speed centrifugation, the pellet was resuspended overnight at 4° C. in 0.05M borate buffer, pH 8.0, 1 mM $Na_2$ EDTA (resuspension buffer). The final pellet was resuspended and used immediately for nucleic acid extraction or stored at −20° C. BNYVV from infected *C. quinoa* and healthy *C. quinoa* extracts used as controls were prepared in the same manner.

Extraction and chromatography of viral RNA:

Viral RNA was extracted with chloroform and phenol in 2X STE by the method described by Sambrook et al., 1989, In: *Molecular Cloning: A Laboratory Manual*, 2d Ed., NY, Cold Spring Harbor Laboratory, with 1% sodium dodecyl sulfate (SDS) and precipitated in three volumes of ethanol at −20° C. and electrophoresed in a 1% agarose formaldehyde denaturing gel in the presence of 0.5 µg/ml of ethidium bromide. Nucleic acid sizes were estimated relative to a 0.24–9.5 kb RNA ladder (Gibco BRL, Gaithersburg, Md.). BNYVV or maize chlorotic mottle virus RNA (4.4 kb) were included as controls.

Nucleic acid extracted from two BSBMV isolates BSBMV-NC and BSBMV-FS separated into four discrete bands with estimated sizes of 6.6, 4.4, and 1.0 kb and 6.7, 4.9, 3.4 and 1.8 kb, respectively. The two larger BSBMV RNAs corresponded roughly in size to those of BNYVV RNAs 1 and 2. The 1.8 kb RNA of BSBMV-FS was approximately the same size as BNYVV RNA 3. The BSBNV 3.4 kc RNA did not correspond in size to any RNA reported for BNYVV but was seen in RNA extracted from the BNYVV control. A faint band at the same location was seen in the virus-free *C. quinoa* preparation, but the band was more intense in virus preparations. In hybridization studies, cDNA probes from nonfractionated BSBMV and BNYVV RNA preparations did not hybridize with the 3.4 kb band.

A BSBMV isolate originally obtained from infected root tissue and purified from *C. quinoa* yielded five RNAs with estimated lengths of 6.7, 4.6, 3.4, 1.8 and 1.4 kb. With the exception of the 3.4 kb band, the RNAs from the root preparation were approximately the size of BNYVV RNAs 1, 2, 3, and 4. The two larger BSBMV RNAs have been detected consistently in different isolates.

Poly A-analysis:

Determination of polyadenylation in the nucleic acid was determined by passing BSBMV-NC nucleic acid (now prepared) through an oligo (dT) cellulose column (Gibco, BRL) according to the manufacturer's instructions. Red clover necrotic mosaic virus and potato virus Y (obtained form Steve Lommel, N.C. State University) were used as non-polyadenylated and polyadenylated controls, respectively. Alternatively, magnetic beads coated with oligo (dT) primers (Promega) were mixed with crude BSBMV-infected *C. quinoa* plant extracts, again following manufacturer's instructions. BNYVV was used as a polyadenylated control. Banding patterns of nucleic acid bound by oligo (dT) in both cases were similar to those produced by BSBMV-NC in the denaturing gel. There was no evidence of a 3.4 kb band.

Viral Protein Analysis:

Purified virus was denatured and the virion protein was separated in a discontinuous 12% SDS-polyacrylamide gel (8×7 cm, Hoefer, San Francisco, Calif.). Capsid molecular weight was estimated to be 22.5 K using a 14.3–200 K molecular weight standard (Gibco BRL). BSBMV capsid protein consistently migrated slightly slower than that of BNYVV.

BSBMV and BNYVV coat proteins separated by SDS-PAGE were transferred to nitrocellulose by electrophoresis. The nitrocellulose was probed with BSBMV IgG (ca. 1 µg/ml, antiserum provided by J. E. Duffus & H. Y. Liu, USDA-ARS, Salinas, Calif.) or BNYVV IgG (1:500, v/v; Biorega-Ag, Chapel Hill, N.C.) and reacted with goat anti-rabbit alkaline phosphatase. Blots were visualized with nitro blue tetrazolium and 5-bromo-4-chloro-3-indolyl phosphate. Proteins reacted with homologous antiserum. No reaction with heterologous antiserum or with healthy *C. quinoa* was detected.

Electron Microscopy:

To concentrate virus particles for electron microscopy, extracts from infected sugar beet leaf tissue were processed through the first high-speed centrifugation of the purification procedure. Carbon-coated grids were incubated one hour at 25° C. on the extract, washed with one drop resuspension buffer and two drops distilled water. Particles were stained with two percent phosphotungstic acid, pH 6.2. Particle width was estimated at 19 nm. Particle lengths were divided into 10 nm intervals. The partial purification likely caused virus particles to fracture, resulting in a wide distribution of particle lengths. Modal lengths occurred at 90, 100, 190 and 250 nm. Lengths are approximately those reported for the three shorter BNYVV particles (Putz, 1977 *J. Gen. Virol.*, 35:397–401), with the exception of the 190 nm peak.

Plant Susceptibility to BSBMV:

Purified BSBMN-NC was mechanically inoculated to *C. quinoa* and maintained by successive transfers. Symptomatic leaf tissue was ground in KPB with 0.02M sodium sulfite and mechanically inoculated to leaf tissue of plants to be tested for susceptibility to BSBMV. Host range test plants mock-inoculated with KPB with sodium sulfite were used as controls. Plants were observed periodically for symptom development at least four weeks. At that time, or at the time symptoms were observed, leaf tissue was back-inoculated to *C. quinoa* to verify symptoms were due to BSBMV infection. If no symptoms were observed by the end of four weeks, asymptomatic tissue was back-inoculated to *C. quinoa* to check for asymptomatic infection. If symptoms that developed on back-inoculated *C. quinoa* were questionable, the *C. quinoa* leaves were tested by DAS-ELISA for the presence of BSBMV.

Thirty-one plant species in 12 families were assayed for susceptibility to BSBMV. The following plants were tested:

Aizoaceae

*Tetragonia tetragoniodes* (Pall.) Kuntze

Amaranthaceae

*Amaranthus hybridus* L.

Asteraceae

*Cichorium endiva* L.

*Helianthus annus* L.

*Lactuca sutiva* L.

Brassicacea

*Brassica oleracea* L. var. botrytis L.

*B. oleracea* L. var. capitata L.

*B. oleracea* L. var. gongylodes L.

*B. rapa* L.

*Raphanus sativus* L.

Chenopodiaceae

*Beta macrocarpa* Guss.,

*B. maritima* L.

*B. vulgaris* L.

*Chenopodium album* L.

*C. quiona* Willd.

*Spinacia oleracea* L.

Cucurbitaceae

*Cirtrulls lanatus* (Thunb.) matsum. and Nakai

*Cucurbita pepo* L.

Fabaceae

*Arachis hypogaea* L.

*Glycine max* (L.) Merr.

*Phaseolus vulgaris* L.

*Vigna unguiculata* (L.) Walp.

Malvaceae

*Gossypium hirsutum* L.

Poaceae

*Sorghum bicolor* (L.) Moench

*Triticum aestivum* L.

*Zea mays* L.

Solanaceae

*Capsicum annuum* L.

*Lycopersicon esculentum* Miller

*Nicotiana tabacum* L. (Samsun and Hicks)

*Solanum melongena* L.

Tropaeolaceae

*Tropaeolum majus* L.

Those plants known to be susceptible to BNYVV were found to be susceptible to BSBMV. Those plants found not susceptible to BSBMV are not known to be susceptible to BNYVV. Host plants and symptoms observed were:

PLANT/SYMPTOMS

*Beta vulgaris* L.—sparse, pale yellow local lesions, occasional pinpoint necrotic local lesions in ringspot patters;

*Chenopodium quinoa* Willd.—diffuse, pale yellow local lesions that sometimes expanded along leaf veins of inoculated leaves, and bright yellow local lesions have been observed in *C. quinoa* inoculated with other BSBMV isolates;

*Chenopodium album* L.—pale yellow local lesions;

*Spinacia oleracea* L.—subtle systemic mottling;

*Beta maritima* L.—necrotic lesions with yellow halos, followed by development of systemic mottling and stunting of new growth;

*Beta macrocarpa* Guss.—tan or purple necrotic local lesions, chlorotic halos around the necrotic lesions in early stages of infection, and some BSBMV isolates became systemic in inoculated plants;

*Tetragonia tetragoniodes* (Pall.) Kuntze—pale yellow local lesions which later became bright yellow and coalesced, and necrosis of the entire leaf often followed.

Results indicate that BSBMV is a multiparticulate rod-shaped virus made up of, depending on the isolate, 2–4 polyadenylated RNAs. The two larger RNAs have been present in all isolates studied. Variation in the number of smaller RNAs may be due to source of host plant tissue used for virus increase (i.e., leaf vs. root tissue), temperature, time of year the isolate was collected or naturally-occurring variation within the population.

BNYVV, as a proposed member of the furovirus group, differs fundamentally from other furoviruses in that it possesses 3'polyadenylated RNA and is composed of more than two particles. The only other multiparticulate rod-shaped virus transmitted by *P. betae* known to infect sugar beet is beet soil-borne virus (BSBV). It consists of two non-polyadenylated RNA species of approximately 3.6 and 3.2 kb, with a possible 6.0 kb RNA (Kaufman, et al. 1992, *Intervirology*, 33:97–102). Because of the size of the RNAs and lack of a poly(A) tail, it is considered more similar to other members of the furovirus group than to BNYVV. No serological cross-selection was detected between BSBMV and BNYVV using polyclonal antibodies in this study. BSBMV is serologically different from BNYVV and causes foliar symptoms in systemically infected sugar beets that are distinct from those caused by BNYVV. Based on particle number and morphology, transmission by *P. betae* and the presence of polyadenylated RNA, it is suggested that BSBMV be considered a member of the furovirus group, more similar to BNYVV than to other furoviruses.

Virus maintenance:

BNYVV and BSBMV isolates were obtained from infected sugar beets from Texas, California, and Nebraska (Table 1). Initial isolate selection was based on serology (ELISA) and diagnostic root and foliar symptoms for BNYVV and BSBMV, respectively. Isolates were maintained in the greenhouse in *Chenopodium quinoa* Willd. by repeated mechanical inoculation or in sugar beet root cultures.

Polymerase chain reaction:

A primer pair was synthesized for BNYVV RNA 1 based on published nucleotide sequence data from European isolates (Bouzoubaa et al., 1987, *J. Gen. Virol.*, 68:615–626. The downstream primer BNYVV 1 (5'TTC ACA AGT CAG TA 3') is complementary to bases 6688 to 6704 of RNA 1 but the sequence is common to all four RNA species of BNYVV. The upstream primer BNYVV 3 (5'AGA TAG TGC TAT AAA CGG 3') is identical to bases 5649 to 5666 and is specific for RNA 1.

Crude nucleic acid extracts or purified BNYVV and BSBMV RNA were used as templates for first strand cDNA synthesis in reverse transcriptase reactions. Extracts from noninfected plants were used as controls. Two microliters of sample were mixed with 0.2M 2-mercaptoethanol, 10 pmol BNYVV 1, 10 mM dNTP's, 3.5 U AMV reverse transcriptase (Boehringer Mannheim), 5 µl 5X reaction buffer, supplied with the enzyme, and H$_2$O to a final volume of 20 µl. The solution was incubated at 40C for one hour, diluted to 40 µl with H$_2$O and boiled five minutes to stop the reaction.

PCR amplification was carried out in 50 µl reactions using 2 µl cDNA, 10 pmol of each primer, 10 mM dNTP's, 2.5 U Taq DNA polymerase (Perkin-Elmer), 5 µl of 10X reaction buffer supplied with the enzyme, and H$_2$O to volume. The mixture was overlaid with 100 µl mineral oil and subjected to 35 cycles consisting of one minute at 94C, one minute at 41C, and two minutes at 72C. During the first and last cycle, the extension step was held at 72C for 10 minutes, and the reaction mixture was held at 4C after the final cycle. PCT products were analyzed by electrophoresis in one percent agarose gels followed by staining with ethidium bromide. In some experiments, BNYVV and BSBMV RNA were mixed and used in the cDNA reaction. Alternatively, cDNA made from the different extracts were mixed and used in PCR.

To verify the identity of amplified products, bands of the expected size were cut from gels and DNA was extracted using the Gene Clean Kit (Biosis 101). Purified DNA was digested with restriction enzymes Dra I, Tha I, Nhe I, and Spe I following manufacturers instructions. Based on the published nucleotide sequence of BNYVV, each of these enzymes was expected to digest the BNYVV PCT product at only one site, with the exception of Dra I with three predicted restriction sites. Digestion products were analyzed by electrophoresis in one percent agarose gels after staining with ethidium bromide.

RESULTS

A PCR product of the expected size was produced by PCR amplification by BNYVV cDNA using two primers BNYW 1 and BNYVV 3. The same product was obtained using either crude nucleic acid extracts or purified virion RNA preparations. Somewhat unexpectedly, a PCR product was also produced when the BNYVV primers and BSBMV cDNA template were used. This product, approximately 1000 bp compared to 1056 bp for the BNYVV product, was produced with all BSBMV isolates tested. However, when BNYVV was mixed with BSBMV, either as RNA samples for first strand cDNA synthesis or as cDNA in PCR, only the BNYVV product was amplified.

When exposed to restriction enzyme digestion, both BNYVV and BSBMV PCR products were digested by Dra I, Nhe I, and Spe I, as predicted from BNYVV nucleotide sequence data. However, Tha I only digested the BSBMV product. When BSBMV cDNA was mixed with BNYVV cDNA and amplified by PCR, the single resulting product was not digested by Tha I, further indicating that only BNYVV cDNA was amplified in mixed samples. In all cases, restriction fragments corresponding to the 5' ends of BNYVV and BSBMV were similar in size, while those corresponding to the 3' end of fragments of BSBMV were smaller than those of BNYVV. These results suggested that the nucleotide sequence of the BSBMV product is quite similar to that of the BNYVV product and that the size difference between the two products is likely due to a small deletion near the 3' end of BSBMV RNA 1.

After determining that primers BNYVV 1 and BNYVV 3 directed amplification of a cDNA product unique for BSBMV, the BSBMV PCR product was cloned to Hinc II digested pGEM3z and partially sequenced from each end by the dideoxy method of Sanger et al. Based on the preliminary nucleotide sequence data, two primers specific for BSBMV were synthesized. The upstream primer BSBMV-1 (5' TAC GCA ACT CAT TGA AAG GTA-3') is identical to bases 66–86 of the BSBMV PCR product and the downstream primer BSBMV-2 (5'-AGA TAA CAC TTG TAA CTC GTC-3') is complementary to bases 737 to 756. Using these primers and BSBMV cDNA from several isolates, the expected PCR product of 691 bp was obtained. The primers BSBMV −1 and −2 did not allow the amplification of BNYVV cDNA, and when BNYVV and BSBMV cDNA were mixed and used in PCR, only the 691 bp product of BSBMV was amplified. This product was digested with Tha I, verifying its origin from BSBMV.

The results of this study support conclusions that BSBMV is very closely related to BNYVV. Primers specifically designed for BNYVV RNA 1 matched BSBMV RNA well enough to allow amplification of a PCR product. However, in the presence of both viruses, the precise match of BNYVV primers with BNYVV templates likely allowed more efficient DNA amplification than with BSBMV templates. Thus, the homologous BNYVV PCR products predominated in PCR reactions with mixtures of BNYVV and BSBMV cDNAs. Furthermore, the BSBMV product had Dra I, Nhe I, and Spe restriction sites in common with the BNYVV PCR product. The BSBMV product was also digested by Tha I, but not the BNYVV product, as predicted. This indicates the nucleotide sequence of the BNYVV isolate used in this study differs from the published sequence of the European isolate in at least one restriction site near the 3' end of RNA 1.

Although genetic variation is likely among isolates of BSBMV, RT-PCR products from different isolates appeared identical. Whether products were amplified using the BNYVV primer pair or BSBMV −1 and −2, the PCR products produced with a given primer pair were apparently identical in size and restriction digestion profile. More importantly, BNYVV and BSBMV were easily detected and differentiated in infected plant tissue. If cDNA made from BSBMV or BNYVV extracts were mixed, the two primer pairs only directed the amplification of the homologous cDNA. Thus, if a plant is infected with both viruses, only one will be detected with a given set of primers. However, if the 1000 bp BSBMV product is amplified using the BNYVV primer pair, no BNYVV is present in the sample. This can be verified by restriction analysis with Tha I.

Example 7

Sugar Beet Plants Tolerant to BNYVV

Sugar beet seeds are coated with viriliferous fungus carrying BSBMV by the seed coating method described for Example 1. Seeds are planted in soil and grow into plants infected with BSBMV, as determined by ELISA or by expression of mild disease symptoms. Subsequent challenge with BNYVV either by mechanical inoculation or by soilborne fungus infection results in sugar beet plants which fail to express severe symptoms of Rhizomania.

Example 8

Transmission of a Foreign Nucleic Acid Sequence to a Host Plant

A foreign gene is incorporated into a host plant susceptible to a soilborne fungus and a virus transmitted by the fungus via the viruliferous fungus coated seed method of the present invention. A foreign nucleic acid sequence, e.g., the DNA sequence encoding the commercially available marker GUS is first incorporated into a virus such as the furovirus serotype BSBMV. This may be accomplished by methods known to those of skill in the art, e.g., by restriction digestion and ligation methods. (See generally, Sambrook et al., 1989, *Molecular Cloning: A Laboratory Manual*, 2d Ed., NY, Cold Spring Harbor Laboratory).

The furovirus is then used to inoculate a host plant, which plant is grown in soil containing a soilborne fungus, such as Polymyxa. The virus infects the fungus, and the fungus-infested plant roots or cystosori are harvested. The powdered viruliferous fungus infested plant roots or cystosori are mixed with an aqueous solution of a polymer such as methyl cellulose, and coated onto seed of a host plant. When planted into soil and permitted to grow, the virus infects the growing plant, thereby transmitting the foreign nucleic acid sequence. The plant tissue is harvested and assayed for the expression of the inserted nucleic acid sequence by known methods, e.g., by ELISA or visual inspection for phenotypic expression.

I claim:

1. A method for protecting plants from severe disease caused by a pathogenic virus comprising the steps of:
    infecting a plant susceptible to severe disease caused by beet necrotic yellow vein virus (BNYVV) with beet soilborne mosaic virus (BSBMV);

wherein the BSBMV infected plant is protected against severe disease caused by BNYVV.

2. The method of claim 1, wherein said BNYVV virus is transmitted to said plant by a soil fungus.

3. The method of claim 1, wherein said plant is a sugar beet plant.

4. The method of claim 2, wherein said soil fungus is Polymyxa.

5. A method for protecting plants from severe disease caused by a pathogenic virus comprising the steps of:

contacting seed of a plant susceptible to severe disease caused by beet necrotic yellow vein virus (BNYVV) with a viruliferous soilborne fungus containing beet soilborne mosaic virus (BSBMV); wherein a plant which grows from said seed becomes infected with said BSBMV virus and is thereby protected against severe disease caused by BNYVV.

6. The method of claim 5, wherein said soilborne fungus is Polymyxa.

7. The method of claim 6, wherein said soilborne fungus is *Polymyxa betae*.

8. The method of claim 3 wherein said contacting comprises planting the seed in soil containing the viruliferous soilborne fungus.

9. The method of claim 3, wherein said contacting comprises coating the seed with a composition comprising said viruliferous soilborne fungus.

10. The method of claim 9 wherein said contacting comprises coating seed with a composition comprising cystosori of said viruliferous fungus.

11. A method for producing seed which will yield plants protected from severe disease caused by a pathogenic virus comprising the steps of:

coating seed of a plant susceptible to severe disease caused by beet necrotic yellow vein virus (BNYVV) with a composition comprising a viruliferous soilborne fungus, which fungus contains beet soilborne mosaic virus (BSBMV);

wherein said coated seed produces a plant which is infected with BSBMV and is thereby protected against severe disease caused by BNYVV.

12. The method of claim 11, wherein said BSBMV virus is transmitted to said plant by a soil fungus.

13. The method of claim 11, wherein said soilborne fungus is Polymyxa.

14. The method of claim 11, wherein said seed produces a sugar beet plant.

15. A method for preparing seed which will yield plants protected from severe disease caused by a pathogenic virus, comprising the steps of:

coating seed of a first plant which is susceptible to severe disease caused by beet necrotic yellow vein virus (BNYVV) with a composition comprising a soilborne fungus obtained from plant roots of a second plant, which second plant is infected with beet soilborne mosaic virus (BSBMV);

wherein a plant which grows from said seed becomes infected with said BSBMV and is thereby protected against severe disease caused by BNYVV.

16. The method of claim 15, wherein said BNYVV virus is transmitted to said first plant by a soil fungus.

17. The method of claim 15, wherein said first plant is a sugar beet plant.

18. The method of claim 15, wherein said soilborne fungus is Polymyxa.

19. A seed composition comprising:

seed of a plant susceptible to severe disease caused by beet necrotic yellow vein virus (BNYVV);

wherein said seed is coated with a viruliferous soilborne fungus infected with beet soilborne mosaic virus (BSBMV);

wherein plants which grow from said seed composition become infected with said BSBMV and are thereby protected against severe disease caused by BNYVV.

20. The coated seed composition of claim 19, wherein said viruliferous soilborne fungus comprises viruliferous cystosori.

21. The coated seed cystosori of claim 19, wherein said BNYVV virus is transmitted to said plants by a soil fungus.

22. The coated seed composition of claim 19, wherein said seed produces a sugar beet plant.

23. The coated seed composition of claim 19, wherein said soilborne fungus is Polymyxa.

24. The seed composition of claim 19, further comprising methyl cellulose to adhere said viruliferous soilborne fungus to said seed.

* * * * *